Figure 1:
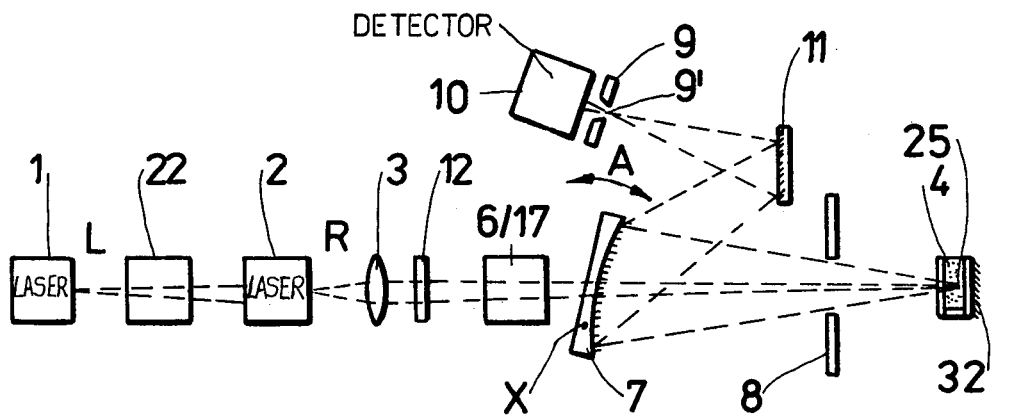

United States Patent [19]

Lucht et al.

[11] Patent Number: 4,461,573
[45] Date of Patent: Jul. 24, 1984

[54] SPECTRAFLUOROMETER ARRANGEMENT

[76] Inventors: Hartmut Lucht, 12, Semmonenweg, 1185 Altglienicke, Berlin; Reiner Wendt, 11, Altheiderstr., 1199 Berlin, both of German Democratic Rep.

[21] Appl. No.: 378,494

[22] Filed: May 18, 1982

[30] Foreign Application Priority Data

Jun. 10, 1981 [DD] German Democratic Rep. ... 230691

[51] Int. Cl.³ .............................................. G01N 21/64
[52] U.S. Cl. .................................. 356/318; 250/458.1; 356/73
[58] Field of Search ................ 356/301, 73, 317, 318, 356/332, 334; 250/458.1, 459.1, 461.1, 461.2

[56]  References Cited
U.S. PATENT DOCUMENTS

| | | | |
|---|---|---|---|
| 3,567,322 | 3/1971 | Brehm et al. | 356/332 |
| 3,753,618 | 8/1973 | Haley | 356/334 |
| 4,351,611 | 9/1982 | Leif | 356/318 |

Primary Examiner—F. L. Evans

[57]  ABSTRACT

The invention relates to a spectral fluorometer arrangement including a laser light source, particularly for use in measuring the luminescence in the course of a qualitative and quantitative determination of a sample material, comprising a beam splitter inserted between said laser light source and a tunable dyestuff laser, at least one collective lens and grey wedge arranged in each of the two beams resulting after said beam splitter, beam fusing means for fusing both beams and positioning the latter in a sample material to be excited. By virtue of the invention a plurality of laser beams can be superimposed in the sample material and can be time correlated.

4 Claims, 3 Drawing Figures

SPECTRAFLUOROMETER ARRANGEMENT

The invention relates to a spectral fluorometer including a laser light-source, particularly for use in measuring the luminescence for a qualitative and quantitative determination of a sample material.

Luminescence measurements are of particular advantage when small quantities of sample materials are investigated with respect to their photophysical and photochemical properties of electronically excited atoms and molecules, respectively.

For luminescence measurements spectral fluorometers are used, where a radiation source of a considerably wide spectral continuum, such as a xenon lamp, is imaged into the entry slit of an excitation monochromator.

The monochromatic light resulting in the exit slit is focused into a sample through a respective lens, thus a sample material is excited in the consequence of which a luminescence results.

The luminescent light is generally focused via further lenses into the entry slit of an emission monochromator under a right angle to the excitation light.

A photodetector arranged subsequent to the exit slit of the arrangement evaluates the radiation.

In a further known arrangement a $N_2$-laser pumps a dyestuff laser, the beam from the latter directly excites the sample. It is also feasible to double the frequency by inserting a KDP crystal.

The luminescent light from the sample is focused under a right angle relative to the exciting light into the entry slit of an emission monochromator via lenses. A photodetector is arranged subsequent to the exit slit of the monochromator.

Such an arrangement is disadvantageous when considerably high absorbing sample material is investigated. The path of beams has to be varied since the excitation of the sample material and the measuring of the luminescence has to be carried out from the same side. The latter is also referred to as incident light measurements.

The previous arrangement does not permit a time correlated excitation through light from two different light sources and of different wavelengths, either.

Furthermore, a simultaneous measurement of the absorption of the sample material is not feasible. Thus, the previous art does not permit to employ luminescence and absorption spectroscopy in a staged excitation procedure.

This, however, is very often necessary since multifold qualitative and quantitative informations about a sample material under examination are very often required apart from the fact that such an excitation procedure produces fluorescent levels with a number of materials which cannot be obtained from the ground level.

It is an object of the present invention to obviate the above disadvantages.

It is a further object of the present invention to provide an arrangement for investigating sample materials which permits a staged and time correlated excitation of said materials and a simultaneous measurement of both, the absorption and the luminescence under incident light and under right angles, that is, between the exciting light and the excited light.

It is still a further object of the invention to provide a spectral fluorometer arrangement which permits an excitation of a sample material by a plurality of laser beams which impinge thereupon from different directions and which are time correlated.

These and other objects are realised in a spectral fluorometer arrangement including a laser light source and a tunable dyestuff laser being pumped by said laser light source, optical directing means for focussing the laser beam into a sample material and means for analysing the radiation emitted from said sample material excited by said dyestuff laser beam.

The arrangement further includes a beam splitter inserted into a path of beams between said laser light source and said dyestuff laser for splitting the light beam into a first and a second beam.

At least one lens and at least one grey wedge are inserted into said first and said second beam; furthermore, beam fusing means are provided in said first and said second beam in the vicinity of said sample material for equally positioning both beams in the sample material to be excited.

The means for analysing the sample material are an emission monochromator and an emission spectrograph, respectively. Advantageously, the beam splitting means is constituted of a rhomboid and a right angle prism. Two of the parallel faces of said rhomboid are substantially at right angles to the incident light beam and the partially reflecting hypotenuse face of said right angle prism being inclined relative to said incident light beam by substantially 45°. The partially reflecting hypotenuse face is substantially in parallel to the two other parallel faces of said rhomboid and in close contact with one of said two other parallel faces.

The incident light beam is both transmitted through said partially reflecting hypotenuse face and reflected to the face of the rhomboid which is in spaced parallel relation to said hypotenuse face where it is reflected in parallel to the transmitted portion.

The dyestuff laser beam after excitation through the transmitted beam portion and the reflected beam portion are superimposed by the beam fusing means in the sample region to be analysed.

Said beam fusing means is constituted in analogy to said beam splitting means, however, in mirror symmetrical spaced relation to the latter.

The dyestuff laser beam is reflected at the partially reflecting face of said beam fusing means inclined by about 45° degree relative to the incident beam, and the reflected beam portion is deviated at a face in parallel to said partially reflecting face of said beam fusing means transmitted by the latter face to impinge upon the sample. It is advantageous to embody the partially reflecting inclined face of said beam fusing means as an air gap which is provided at the place of the reflection and which is included in and between the rhomboid on the one hand and the hypotenuse face of the right angle prism on the other hand, said rhomboid and said hypotenuse face forming a close contact face except for the air gap inclusion.

The reflected beam portion is deviated at the rhomboid face which is in parallel to the air gap inclusion and is transmitted through the close contact face.

It is a further advantage when an optically controllable delay means is inserted between the beam splitting means and the beam fusing means into one of the two beams in order to control the time correlation between the $N_2$-laser and the tunable dyestuff laser.

In order to obtain a shortwave excitation of the sample material a suitable crystal for optical frequency doubling is inserted between the dyestuff laser and the beam fusing means into the respective beam.

By virtue of the inventional spectralfluorometer arrangement a considerably sensitive measurement of both, luminescence and absorption is feasible in a simple and staged excitation. The time correlation is adjustable as desired. The luminescence measurement is feasible in incident light as well as at right angles, which permits the measurement of a fluorescence polarisation.

The required mechanical changeovers of the measuring arrangement are easy to handle.

Figure 2:
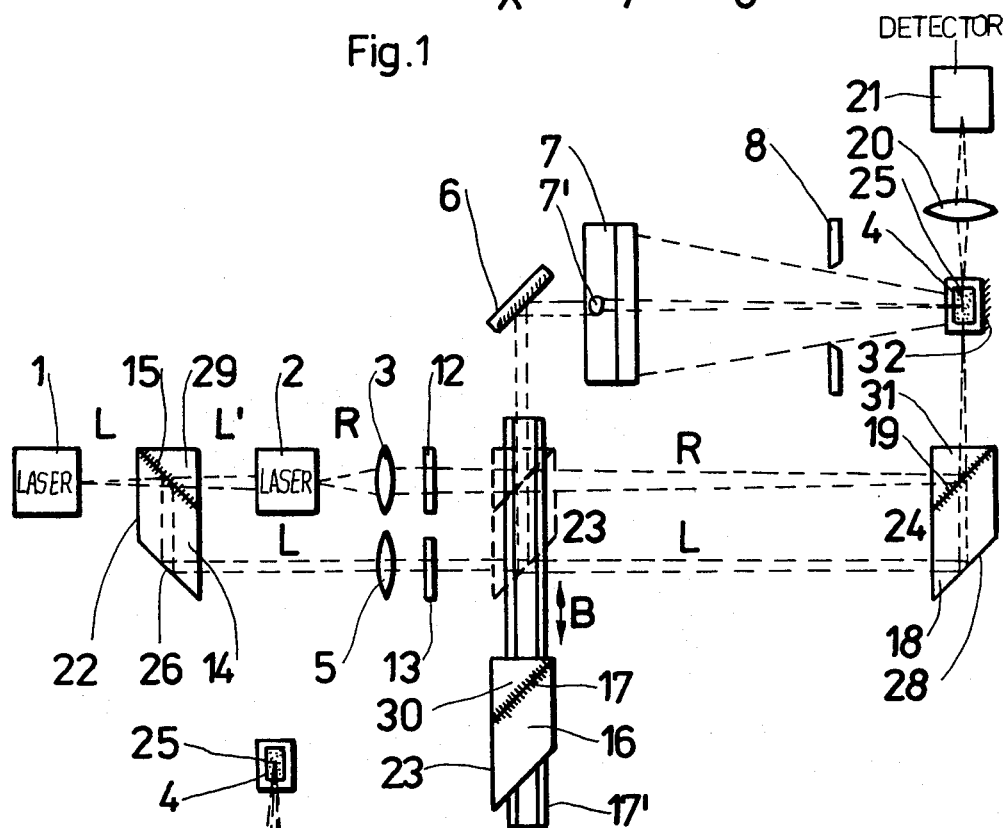
Figure 3:
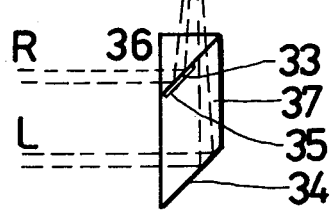

In order that the invention may be more readily understood reference is made to the accompanying drawings which illustrate diagrammatically and by way of example two embodiments thereof and where FIG. 1 is a schematical side view of a spectral fluorometer arrangement, FIG. 2 is a schematical top view of the spectral fluorometer arrangement of FIG. 1, and FIG. 3 an embodiment of a beam fusing means of the spectral fluorometer arrangement.

In FIG. 1 a laser light source 1, for example, a $N_2$ laser emits a beam L in which a beam splitting means 22 is inserted followed by a dyestuff laser 2, a collective lens 3, a grey wedge 12 and deviating means 6 and 17, respectively, which laterally displace and direct a laser beam R upon an object point 25 of a sample material 4, after passage through an opening 7′ (FIG. 2) of a concave grating 7 belonging to an emission monochromator and an aperture 8 for the luminescence light. A measuring arrangement for measuring the luminescence excited in the sample material 25 comprises the aperture 8, the holographic concave grating 7, a deviating reflector 11, an aperture 9, and a photodetector 10.

In operation, the laser light source 1 produces a laser beam L which is directed upon the beam splitter 22 which splits the laser beam L into a first portion L′ and a second portion L.

About 10 percent of the radiation is coupled out of the laser beam L by the beam splitter 22.

The first portion L′ pumps the tunable dyestuff laser 2 which emits a laser radiation R.

The latter is focussed by the collective lens 3 upon the sample 25 after passage through the grey wedge 12 and the deviating means 6 and 17 which laterally displace the laser radiation R, which passes the opening 7′ in the center of the concave grating 7 which is part of an emission monochromator and after passage through the aperture 8 impinges upon a definite range (object point) 25 of the sample material 4 and excites the latter to emit a luminescence which, in reverse direction to R passes the aperture 8 and impinges upon the holographic grating 7. The aperture 8 and the grating 7 define an opening ratio of 1:3 for the indication of the luminescence.

Depending on the inclination of the grating 7 relative to the incident luminescence radiation the luminescence light of a definite wavelength is reflected at the grating 7 to the reflector 11 which directs the luminescence light upon the exit slit of the detector 10.

The desired wavelength in the exit slit 9 is produced by rotating the grating 7 about an axis of rotation X, the rotational movement is actuated by not shown means in the direction indicated by a double arrow A by a respective position of the object point 25 of the grating 7 relative to the position of an image point 9′ in the exit slit 9, which ensures that the astigmatism in the exit slit 9 is low and the spectral resolution considerably high over a wide spectral range.

The holographic grating 7 is provided with layers which permit a wavelength variation when the grating is respectively rotated.

In FIG. 2 the fluorometer of FIG. 1 is shown in top view. The laser light source 1 produces the laser beam L which is split by a partially reflective layer 15 of the beam splitting means 22.

The latter is composed of a rhomboid 14 and a right angle prism 29, two parallel faces of said rhomboid 14 are substantially at right angles to the incident laser beam L, whereas the partially reflective layer 15 which is inclined relative to the beam L by substantially 45° is both, the hypotenuse face of the right angle prism 29 and the one of the two other parallel faces of said rhomboid, the other face 26 of said two other parallel faces is a reflective one. The laser beam L is split into a first portion which is transmitted through the face 15 and pumps the dyestuff laser 2 to produce a laser radiation R and into a second portion L which is deflected by said layer 15 and impinges upon the face 26 where it is again reflected and leaves the beam splitting means 22 in parallel but spaced relation to said first portion R to be focused by a collective lens and a grey wedge 13 and deviated by a reflective face 27 of a beam fusing means 23 and the deviating reflector 6 upon the object point 25 of the sample material 4.

The beam fusing means 23 is constituted in analogy to the beam splitting means 22 of a rhomboid 16 and a right angle prism 30 which are arranged in analogy, however, mirror symmetrical relation to the beam splitting means 22 in both, the second portion L of the laser beam and in the dyestuff laser radiation R.

Hence, the partially reflective layer 17 is transmissive to the laser radiation L from the $N_2$-laser but reflective to the dyestuff laser radiation R. Thus, the second portion of the radiation L and the radiation R are equally positioned after the layer 17. The beam fusing means 23 is shown in dashed lines inserted into the beams L and R to indicate that it is removable from out of the dashed lines position into the heavy line position by a displacement means 17′, the directions of movement being indicated by a double arrow B. When the beam fusing means 23 is removed from out of the beams L and R, the laser beam R impinges upon a partially reflecting layer 19 which is inclined relative to the beam R by an angle of 45° and which belongs to a beam fusing means 24 constituted in analogy to the beam fusing means 23 but positioned adjacent the sample material 4.

The dyestuff laser beam R is folded about 90° at said layer 19 and directed into the sample material 4. The partially reflecting layer 19 is reflective to the wavelengths of the radiation R emitted from the dyestuff laser 2 and transmissive to the $N_2$-laser radiation L.

The latter impinges upon a reflecting face 28 (in analogy to the face 27 of the beam fusing means 23) of the beam fusing means 24 and is reflected at right angles through the layer 19 to impinge upon the object point 25 of the sample material 4. After the layer 19 both radiations L and R substantially coincide.

The sample material 4 is excited at right angles to the measuring direction of the luminescence light emitted from the sample 4, that is, the exciting radiations R and L and the luminescence light include a right angle at the place of the sample 4.

Since the $N_2$-laser is a pulsed laser, it is feasible to vary the time relation between both laser beam pulses R and L by inserting optical delay means into one of the two laser beams.

It is also feasible to obtain a frequency doubling by inserting a KDP-crystal into the laser beam R subsequently to the dyestuff laser 2.

In order to perform an absorption measurement of the sample material 4 a collective lens 20 is arranged subsequent to the sample material 4 in the focus of which a detector 21 is arranged.

In FIG. 3 a beam fusing means 36 is shown which does not require expensive layer materials as in the event of the beam fusing means 23 and 24. The beam fusing means is constituted of a rhomboid prism 37 and a right angle prism 36.

The opposing faces 33 and 34 are not parallel but include an acute angle which is so selected that the laser beams R and L intersect in the object point 25 of the sample 4.

The hypotenuse face of the right angle prism 36 and one face of the rhomboid 33 are in close contact except for a portion which is occupied by an inbetween air gap 35. In operation, the dyestuff laser beam R enters the right angle prism portion 36 of the beam fusing means and is reflected at the air gap 35 to impinge upon the sample material 4 non-parallel to the laser beam L which is reflected at the face 34 and transmitted through the hypotenuse face 33 to impinge upon the sample 4, where the beams R and L intersect in the object point 25 of the sample material 4.

We claim:

1. A spectral fluorometer arrangement for the qualitative and quantitative determination of a luminescence radiation emitted from a sample material,
   comprising in mutual optical alignment,
   a laser for emitting a first laser beam,
   a beam splitter including a first partially reflective, partially transmissive beam splitting face arranged in and inclined relative to said laser beam by substantially 45°,
      said beam splitter having a further inclined and reflective face in spaced substantially parallel relation to said first beam splitting face,
      said beam splitter being for splitting said laser beam into a first beam portion and into a second beam portion,
   a dyestuff laser,
   at least one first optical beam focusing means,
   at least one second beam focusing means,
   first and second beam intensity controling means,
   a first beam fusing and deviating means,
   a second beam fusing and deviating means,
      said first beam portion being for pulsing said dyestuff laser,
      said dyestuff laser being for producing a second laser beam,
      said beam splitting face and said further reflective face being for directing said second beam portion in parallel to said second laser beam,
      said first beam focusing means and said second beam focusing means, and said first and said second beam intensity controling means being arranged in said second laser beam and in said second beam portion, respectively,
   a wavelength variation means having a central opening, and
   an axis of rotation,
   said axis of rotation being horizontal and at right angles to said first laser beam,
   a sample material to be analysed,
   a beam directing means,
   a first detector means,
   a second detector means,
   a means for displacing said first beam fusing and deviating means into and out of, respectively, said second laser beam and said second beam portion,
      said second beam fusing and deviating means being arranged subsequent to said first beam fusing and deviating means and adjacent said sample material,
      said first beam fusing and deviating means being for fusing and directing said second laser beam and said second beam portion through said opening of said wavelength variation means upon said sample material, said second beam fusing and deviating means, when said first beam fusing and deviating means being removed from said second laser beam and said second beam portion,
      being for directing said second laser beam and said second beam portion to said sample material,
      said second laser beam and second beam portion being for producing a first and a second luminescent radiation of said sample material,
      said first and said second luminescent radiation including a right angle,
      said wavelength variation means and said beam directing means being for directing said first luminescent radiation to said first detector means,
      said second detector means being arranged subsequent to said sample material,
      said second detector means being for detecting said second luminescent radiation from said sample material.

2. A spectral fluorometer arrangement as claimed in claim 1, wherein said second beam fusing and deviating means has a partially transmissive and reflective face inclined to said second laser beam by about 45°, and a second reflective face in spaced parallel relation to said partially transmissive and reflective face, said second reflective face deviating said second beam portion by substantially 90°, said partially reflective and transmissive face deviating said second laser beam by substantially 90° and transmitting the deviated second beam portion, said second beam portion and said second laser beam substantially coinciding in said sample material subsequent to said partially reflective and transmissive face.

3. A spectral fluorometer arrangement as claimed in claim 2, wherein said partially reflective and transmissive face is partially constituted of and entirely including an oblong air gap extending along a portion of said face, said air gap being reflective to said second laser beam, the other part of said face being transmissive for said second beam portion.

4. A spectral fluorometer arrangement as claimed in claim 2, wherein said first beam fusing and deviating means is constituted in analogy to said second beam fusing and deviating means and further includes a beam folding means arranged in said second laser beam and said second beam portion between said first beam fusing and deviating means and said wavelength variation means, inclined by substantially 45° relative to said second laser beam and said second beam portion.

* * * * *